United States Patent [19]

Kaye et al.

[11] Patent Number: 4,461,718

[45] Date of Patent: Jul. 24, 1984

[54] WAVELENGTH ACCURACY TEST SOLUTION

[75] Inventors: Wilbur I. Kaye, Corona Del Mar; Lilla S. Sun, Seal Beach; John C. Anderson, Burbank, all of Calif.

[73] Assignee: Beckman Instruments, Inc., Fullerton, Calif.

[21] Appl. No.: 330,972

[22] Filed: Dec. 15, 1981

[51] Int. Cl.$^3$ .................. C09K 3/00; G01N 31/00; G01N 33/00
[52] U.S. Cl. ................... 252/408.1; 252/1; 250/252.1; 436/8; 436/19
[58] Field of Search .............. 252/408.1, 1; 250/252.1; 436/8, 19

[56] References Cited

PUBLICATIONS

West, "Practical Standards for UV Absorption . . . ", American Laboratory, Mar. 1977, pp. 37–49.
Merck, Index, 8th Ed., 1968, p. 798, Merch & Co., Inc., "Perchloric Acid".
Bernard, "The Liq-QA-Pac TM Quality Assurance Kit for use with DU ®-6 and DU ®-7 UV-Vis Spectrophotometers", Technical Information, T1544-UV-8-3-3, Beckman Instruments, Inc., 1983.
Alfa Catalog 1982, pp. 378, 457, Alfa Products, Thiokol/Ventron Division.
Frings, "Calibration and Monitoring . . . ", *Clin. Chem.*, vol. 25, No. 6, 1979.
Frings, "Convenient Method . . . ", *Clin. Chem.*, vol. 22, No. 1, 1976.

*Primary Examiner*—Teddy S. Gron
*Assistant Examiner*—Catherine S. Kilby
*Attorney, Agent, or Firm*—R. J. Steinmeyer; R. R. Meads; R. S. Frieman

[57] ABSTRACT

A wavelength calibration solution comprising from about 0.025 to about 0.140 molar neodymium and from about 0.135 to about 0.550 molar samarium, wherein the neodymium is present as a neodymium ionized constituent and the samarium is present as a samarium ionized constituent.

A method for checking the wavelength accuracy of spectrometers or spectrophotometers of the type comprising measuring the absorbance (A) or percent transmittance (% T) of a wavelength calibration check solution versus a blank at more than one wavelength. The method is characterized in that the above solution is employed therein as the wavelength calibration check solution.

5 Claims, No Drawings

WAVELENGTH ACCURACY TEST SOLUTION

BACKGROUND OF THE INVENTION

1. Field of the Invention

This invention relates to a calibrator and, more particularly, to a wavelength calibration solution.

2. Description of the Prior Art

Frings et al. (1) report that the percentage of quantitative analyses performed in the clinical laboratory that involve spectrophotometry or colorimetry was estimated in 1969 to be possibly more than 95% (2). Most laboratories continue to rely heavily upon spectrometers or spectrophotometers for the majority of their analyses. Maintenance of properly functioning spectrometers and spectrophotometers is an obvious prerequisite to the assurance of accurate analytical results. Moreover, the increased regulation of clinical laboratory by governmental and professional agencies mandates that laboratory personnel periodically verify that a given spectrometer or spectrophotometer is functioning properly. By periodically inspecting spectrometric and spectrophotometric functions, subtle or gradual degradations in performance can be detected before they significantly affect analytical results. As a minimum, these inspections should include, inter alia, a check of wavelength calibration.

With respect to wavelength calibration, periodic checks are necessary to insure that the instrument wavelength accurately reflects the wavelength of energy passing through the exit slit of the monochromators. Several methods are available for checking wavelength accuracy of a spectrometer or a spectrophotometer. These methods include (a) replacing the source lamp with a radiant energy source which has strong emission lines at well defined wavelengths; (b) using rare earth glass filters; and (c) using solutions such as samarium oxide. Irrespective of the method of wavelength calibration, calibration at more than one wavelength is required for proper calibration of the instrument.

In general, the wavelength calibration solution technique involves measuring absorbance (A) or percent transmittance (%T) of the wavelength calibration check solution versus a blank (e.g., water) at more than one wavelength.

Prior art solutions employed to check wavelength accuracy have characteristic wavelength peaks which are not sufficiently separated to enable one to calibrate the instrument over a sufficiently wide spectral range. For example, holmium oxide has characteristic peaks at 536.4 nm, 418.5 nm, and 360.8 nm. In addition, the peaks at 418.5 and 536.4 nm are not easily identifiable due to lack of peak intensity.

In contrast, it would be very desirable to employ a solution with at least two very easily identifiable, sharp peaks which are separated by over 100 nms.

SUMMARY OF THE INVENTION

In accordance with the present invention, there is provided a novel wavelength calibration check solution. More particularly, the calibration check solution of the instant invention comprises from about 0.025 to about 0.140 molar neodymium, and from about 0.135 to 0.550 molar samarium, the neodymium and samarium being present as a neodymium ionized constituent and a samarium ionized constituent, respectively.

The wavelength calibration solution of the instant invention has characteristic peaks at $400\pm2$ nm and $576\pm2$ nm. In addition to being separated by over 100 nms, these peaks are sharp and easily identifiable.

In addition, the instant invention also comprises an improved method for checking the wavelength accuracy of spectrometers or spectrophotometers. The method of the instant invention is of the type comprising measuring the absorbance (A) or percent transmittance (%T) of a wavelength calibration check solution versus a blank at more than one wavelength. The improved method of the instant invention is characterized in that the above described wavelength calibration check solution is employed therein.

Still other features and attendant advantages of the present invention will become apparent to those skilled in the art from a reading of the following detailed description of the preferred embodiments.

DESCRIPTION OF THE PREFERRED EMBODIMENTS

The wavelength calibration check solution of the instant invention comprises from about 0.025 to about 0.140 molar neodymium, and from about 0.135 to about 0.550 molar samarium, the neodymium being present as a neodymium ionized constituent and the samarium being present as a samarium ionized constituent. Preferably, the wavelength calibration check solution comprises from about 0.025 to about 0.090 molar neodymium and from about 0.245 to about 0.305 molar samarium. Optimally, the wavelength calibration check solution comprises from about 0.065 to 0.075 molar neodymium and from about 0.270 to about 0.280 molar samarium.

Essentially any neodymium compound and samarium compound having sufficient solubility can be employed in the solution of the present invention. Preferably, the neodymium compound is neodymium chloride and the samarium compound is samarium chloride.

The wavelength calibration check solution can optionally also comprise any composition which is capable of enhancing the solubilization of the neodymium and samarium compounds. This optional composition must be devoid of any substantial absorption at both 400 and 576 nanometers (nm) in order to avoid interfering with the calibration procedure. Up to 0.02 normal (N) hydrochloric acid (HCl) can be used as such solubilization enhancer. Preferably, the solution should comprise from about 0.004 to 0.006N HCl.

The wavelength calibration check solution can be made by any convenient process known to those skilled in the art. For example, one can add a suitable amount of solubilization enhancing composition to a given amount of water, preferably distilled water. Subsequently, one can add the appropriate neodymium and samarium compounds to this solution with sufficient mixing to assure complete solubilization of these compounds.

The wavelength calibration method of the instant invention for checking the wavelength accuracy of spectrometers or spectrophotometers of the instant invention is of the type which comprises measuring A or %T of a wavelength calibration check solution versus a blank, e.g., water, at more than one wavelength. The method of the instant invention is characterized in that the above described wavelength calibration check solution is employed and the measurements are made at approximately $400\pm2$ and $576\pm2$ nm.

The following examples are provided for the purpose of further illustration only and are not intended to be limitations on the disclosed invention.

EXAMPLE 1

Hydrochloric acid (12N, 0.8 ml) was added to two liters of distilled water to form a 0.005N HCl solution. Neodymium chloride ($NdCl_3 \cdot 6H_2O$; 50.05 gm) and 200.0 gm of samarium chloride ($SmCl_3 \cdot 6H_2O$) were then added to the 0.005N HCl solution with sufficient mixing to stabilize all constituents. The resulting solution contained approximately 0.0697M $NdCl_3$ and approximately 0.274M $SmCl_3$.

EXAMPLE 2

A spectrophotometer was turned on and allowed to warm-up to operating temperature. An aliquot of solution prepared in Example 1 was placed in the spectrophotometer's sample compartment's cuvette and a water blank was placed in the reference component's cuvette. The absorbance was measured at 576±2 nm and then at 400±2 nm.

The data obtained from this procedure indicated that the wavelength of the particular spectrophotometer being checked was correct.

Based on this disclosure, many other modifications and ramifications will naturally suggest themselves to those skilled in the art. These are intended to be comprehended as within the scope of this invention.

Bibliography

1. Frings et al., *Clin. Chem.*, 25(6):1013–1017 (1979).
2. Rand, *Clin. Chem.*, 15:839–863 (1969).

The embodiments of the invention in which an exclusive property or privilege is claimed are defined as follows:

1. A solution comprising:
 (a) from about 0.025 to about 0.140 molar neodymium;
 (b) from about 0.135 to about 0.550 molar samarium; and
 (c) up to about 0.02 N hydrochloric acid; wherein said neodymium is present as a neodymium ionized constituent and said samarium is present as a samarium ionized constituent, said neodymium ionized constituent being ionized neodymium chloride and said samarium ionized constituent being ionized samarium chloride.
2. The solution of claim 1 comprising
 (a) from about 0.050 to about 0.090 molar neodymium and
 (b) from about 0.245 to about 0.305 molar samarium.
3. The solution of claim 1 comprising:
 (a) from about 0.065 to about 0.075 molar neodymium; and
 (b) from about 0.270 to about 0.280 molar samarium.
4. The solution of claim 2 comprising from about 0.004 to about 0.006N hydrochloric acid.
5. The solution of claim 3 comprising from about 0.004 to about 0.006N hydrochloric acid.

* * * * *